(12) United States Patent
Ohnishi et al.

(10) Patent No.: US 7,416,736 B2
(45) Date of Patent: Aug. 26, 2008

(54) ANTIMICROBIAL COMPOSITIONS

(75) Inventors: Toshimasa Ohnishi, Hyogo (JP); Ikuya Tanaka, Hyogo (JP)

(73) Assignee: Janssen Pharmaceutica N.V. (BE)

( * ) Notice: Subject to any disclaimer, the term of this patent is extended or adjusted under 35 U.S.C. 154(b) by 674 days.

(21) Appl. No.: 10/469,772

(22) PCT Filed: Mar. 4, 2002

(86) PCT No.: PCT/EP02/02368

§ 371 (c)(1),
(2), (4) Date: Sep. 4, 2003

(87) PCT Pub. No.: WO02/076209

PCT Pub. Date: Oct. 3, 2002

(65) Prior Publication Data

US 2004/0171600 A1 Sep. 2, 2004

(30) Foreign Application Priority Data

Mar. 6, 2001 (JP) .............................. 2001-61158

(51) Int. Cl.
  *A01N 25/00* (2006.01)
  *A01N 55/02* (2006.01)
  *A61K 31/555* (2006.01)
(52) U.S. Cl. ....................... 424/405; 514/184
(58) Field of Classification Search .......... 424/405; 514/184
See application file for complete search history.

(56) References Cited

U.S. PATENT DOCUMENTS

| | | | | |
|---|---|---|---|---|
| 3,583,999 A | * | 6/1971 | Damico | 546/290 |
| 3,892,760 A | * | 7/1975 | Hooks et al. | 546/261 |
| 4,396,766 A | * | 8/1983 | Farmer et al. | 546/6 |
| 5,540,860 A | * | 7/1996 | Hosseini et al. | 516/66 |
| 5,712,275 A | * | 1/1998 | Van Gestel | 514/222.5 |
| 5,777,110 A | * | 7/1998 | Davis et al. | 544/2 |
| 5,922,113 A | * | 7/1999 | Van Gestel | 106/18.33 |
| 6,143,311 A | * | 11/2000 | Chikusa et al. | 424/405 |

FOREIGN PATENT DOCUMENTS

| | | | | |
|---|---|---|---|---|
| GB | 1263581 A | * | 2/1972 | |
| JP | 11217308 | | 8/1999 | |
| JP | 11217308 A | * | 8/1999 | |
| JP | 2000053510 A | * | 2/2000 | |
| JP | 2000191412 A | * | 7/2000 | |
| JP | 2000273003 A | * | 10/2000 | |
| JP | 2000302601 A | | 10/2000 | |
| JP | 2001213708 A | * | 8/2001 | |
| WO | WO 9506043 A1 | * | 3/1995 | |
| WO | WO 99/18795 A1 | | 4/1999 | |
| WO | WO 9918795 A1 | * | 4/1999 | |
| WO | WO 00/32371 A1 | | 6/2000 | |
| WO | WO 0032371 A1 | * | 6/2000 | |

* cited by examiner

*Primary Examiner*—Sreeni Padmanabhan
*Assistant Examiner*—Kendra D Carter

(57) ABSTRACT

This invention concerns antimicrobial compositions that are useful for industrial applications. More specifically, it concerns antimicrobial compositions that, by combining 3-benzo[b]thiene-2-yl-5,6-dihydro-1,4,2-oxathiazine-4-oxide and one or more of 1-[[(3-iodo-2-propynyl)oxy]methoxy]-4-methoxy benzene, 1-chloro-4-[[(3-iodo-2-propynyl)oxy]methoxy] benzene, Zinc 2-pyridine thiol-1-oxide, Copper 2-pyridine thiol-1-oxide, 2-pyridine thiol-1-oxide sodium salt, 2,2-dithio-bis(pyridine-1-oxide), 2-methylthio-4-t-butyl amino-6-cyclopropyl amino-s-triazine, 3-iodo-2-propynyl butylcarbamate (IPBC), 2-(n-octyl)-3(2H)-isothiazolone (OIT), 4,5-dichloro-2-(n-octyl)-3(2H)-isothiazolone (DCOIT), 2,4,5,6-tetrachloro-1,3-benzenedicarbonitrile (chlorothalonil), 1,1-dichloro-N-[(dimethylamino)sulfonyl]-1-fluoro-N-phenyl-methanesulfenamide (dichlofluanid), or 1,1-dichloro-N-[(dimethylamino)sulfonyl]-1-fluoro-N-(4-methylphenyl)-methanesulfenamide (tolylfluanid) have the synergistic effect of these compounds.

5 Claims, No Drawings

ANTIMICROBIAL COMPOSITIONS

CROSS REFERENCE TO RELATED APPLICATIONS

This application is the national stage of Application No. PCT/EP02/02368, filed Mar. 4, 2002, which application claims priority from Japanese Application No. 2001-61158, filed Mar. 6, 2001.

This invention concerns antimicrobial compositions that are useful for industrial applications. More specifically, it concerns antimicrobial compositions that, by combining 3-benzo[b]thiene-2-yl-5,6-dihydro-1,4,2-oxathiazine-4-oxide and one or more of 1-[[(3-iodo-2-propynyl)oxy]methoxy]-4-methoxy benzene, 1-chloro-4-[[(3-iodo-2-propynyl)oxy]methoxy] benzene, Zinc 2-pyridine thiol-1-oxide, Copper 2-pyridine thiol-1-oxide, 2-pyridine thiol-1-oxide sodium salt, 2,2-dithio-bis(pyridine-1-oxide), 2-methylthio-4-t-butyl amino-6-cyclopropyl amino-s-triazine, 3-iodo-2-propynyl butylcarbamate (IPBC), 2-(n-octyl)-3(2H)-isothiazolone (OIT), 4,5-dichloro-2-(n-octyl)-3(2H)-isothiazolone (DCOIT), 2,4,5,6-tetrachloro-1,3-benzenedicarbonitrile (chlorothalonil), 1,1-dichloro-N-[(dimethylamino)sulfonyl]-1-fluoro-N-phenyl-methanesulfenamide (dichlofluanid), or 1,1-dichloro-N-[(dimethylamino)sulfonyl]-1-fluoro-N-(4-methylphenyl)-methanesulfenamide (tolylfluanid) have the synergistic effect of these compounds.

Inorganic or organic compounds that contain mainly mercury, tin, copper, and other heavy metals (hereafter called "heavy-metal compounds") have been widely used as antimicrobial agents for industrial products and industrial raw materials. But the high toxicity of these heavy-metal compounds poses the danger of adversely affecting the human body. In addition, heavy-metal compounds are not suitable for use as antimicrobial agents because of the fear that heavy-metal compounds may lead to environmental destruction.

The many non-metallic antimicrobial agents that have been developed to solve such problems of heavy metal compounds (for example, organic iodine compounds, nitrile compounds, isothiazolone compounds, benzimidazole compounds, pyrithione compounds) have selectivity in their antimicrobial spectrum. Thus even if these non-metallic antimicrobial agents are applied to industrial products or industrial raw materials, in particular organic materials (for example, fibre, paint, adhesives, etc.), micro-organisms on which these antimicrobial agents have little or no effect will grow and propagate, thus allowing the occurrence of contamination of industrial products, etc. or a change in the quality (for example, degradation) of industrial raw materials. Therefore satisfactory antimicrobial effect cannot be obtained by conventional antimicrobial compositions.

Thus attempts have been made to expand the antimicrobial spectrum and increase the antimicrobial effect by combining two or more antimicrobial agents. But usually either the effect of only one of the antimicrobial agents appears, or only an additive effect is obtained.

The purpose of this invention, which is intended to solve the above problems, is to provide antimicrobial compositions that are highly safe, are very effective, and have a wide antimicrobial spectrum.

As a result of diligent study to solve the above problems, the inventors of this invention found that an unexpected synergistic effect is obtained by combining with 3-benzo[b]thiene-2-yl-5,6-dihydro-1,4,2-oxathiazine-4-oxide one or more of the following compounds (a)-(m):

(a) 1-[[(3-iodo-2-propynyl)oxy]methoxy]-4-methoxy benzene
(b) 1-chloro-4-[[(3-iodo-2-propynyl)oxy]methoxy] benzene
(c) Zinc 2-pyridine thiol-1-oxide
(d) Copper 2-pyridine thiol-1-oxide
(e) 2-pyridine thiol-1-oxide sodium salt
(f) 2,2-dithio-bis(pyridine-1-oxide)
(g) 2-methylthio-4-t-butyl amino-6-cyclopropyl amino-s-triazine (irgarol)
(h) 3-iodo-2-propynyl butylcarbamate (IPBC)
(i) 2-(n-octyl)-3(2H)-isothiazolone (OIT)
(j) 4,5-dichloro-2-(n-octyl)-3(2H)-isothiazolone (DCOIT)
(k) 2,4,5,6-tetrachloro-1,3-benzenedicarbonitrile (chlorothalonil)
(l) 1,1-dichloro-N-[(dimethylamino)sulfonyl]-1-fluoro-N-phenyl-methanesulfenamide (dichlofluanid)
(m) 1,1-dichloro-N-[(dimethylamino)sulfonyl]-1-fluoro-N-(4-methylphenyl)-methanesulfenamide (tolylfluanid).

That is, they arrived at the perfection of this invention having discovered that by combining 3-benzo[b]thiene-2-yl-5,6-dihydro-1,4,2-oxathiazine-4-oxide and the above compounds (a)-(m), one obtains antimicrobial compositions that are more effective, and have a wider antimicrobial spectrum, than if each compound is used singly.

This invention provides antimicrobial composition comprising 3-benzo[b]thiene-2-yl-5,6-dihydro-1,4,2-oxathiazine-4-oxide and one or more of the following compounds (a)-(m):

(a) 1-[[(3-iodo-2-propynyl)oxy]methoxy]-4-methoxy benzene
(b) 1-chloro-4-[[(3-iodo-2-propynyl)oxy]methoxy] benzene
(c) Zinc 2-pyridine thiol-1-oxide
(d) Copper 2-pyridine thiol-1-oxide
(e) 2-pyridine thiol-1-oxide sodium salt
(f) 2,2-dithio-bis(pyridine-1-oxide)
(g) 2-methylthio-4-t-butyl amino-6-cyclopropyl amino-s-triazine (irgarol)
(h) 3-iodo-2-propynyl butylcarbamate (IPBC)
(i) 2-(n-octyl)-3(2H)-isothiazolone (OIT)
(j) 4,5-dichloro-2-(n-octyl)-3(2H)-isothiazolone (DCOIT)
(k) 2,4,5,6-tetrachloro-1,3-benzenedicarbonitrile (chlorothalonil)
(l) 1,1-dichloro-N-[(dimethylamino)sulfonyl]-1-fluoro-N-phenyl-methanesulfenamide (dichlofluanid)
(m) 1,1-dichloro-N-[(dimethylamino)sulfonyl]-1-fluoro-N-(4-methylphenyl)-methanesulfenamide (tolylfluanid).

Preferably the weight ratio of above 3-benzo[b]thiene-2-yl-5,6-dihydro-1,4,2-oxathiazine-4-oxide and above compounds (a)-(m) should be in the range 20:1 to 1:20. More preferably, the weight ratio of above 3-benzo[b]thiene-2-yl-5,6-dihydro-1,4,2-oxathiazine-4-oxide and above compounds (a)-(m) should be in range 5:1 to 1:5.

The technical term "antimicrobial composition" used in this specification means a composition that has the effect of inhibiting the growth of bacteria, fungi, yeast, algae, etc. or killing these micro-organisms.

A. Composition of the Invention

A.1. Effective Components

The antimicrobial compositions of this invention comprise as its effective components 3-benzo[b]thiene-2-yl-5,6-dihydro-1,4,2-oxathiazine-4-oxide and one or more of the following compounds (a)-(m):

(a) 1-[[(3-iodo-2-propynyl)oxy]methoxy]4-methoxy benzene (b) 1-chloro-4-[[(3-iodo-2-propynyl)oxy]methoxy] benzene
(c) Zinc 2-pyridine thiol-1-oxide
(d) Copper 2-pyridine thiol-1-oxide
(e) 2-pyridine thiol-1-oxide sodium salt
(f) 2,2-dithio-bis(pyridine-1-oxide)
(g) 2-methylthio-4-t-butyl amino-6-cyclopropyl amino-s-triazine (irgarol)
(h) 3-iodo-2-propynyl butylcarbamate (IPBC)
(i) 2-(n-octyl)-3(2H)-isothiazolone (OIT)
(j) 4,5-dichloro-2-(n-octyl)-3(2H)-isothiazolone (DCOIT)
(k) 2,4,5,6-tetrachloro-1,3-benzenedicarbonitrile (chlorothalonil)
(l) 1,1-dichloro-N-[(dimethylamino)sulfonyl]-1-fluoro-N-phenyl-methanesulfenamide (dichlofluanid)
(m) 1,1-dichloro-N-[(dimethylamino)sulfonyl]-1-fluoro-N-(4-methylphenyl)-methanesulfenamide (tolylfluanid).

3-Benzo[b]thiene-2-yl-5,6-dihydro-1,4,2-oxathiazine-4-oxide can be synthesized by, for example, the method described in JP-B2-2761441.

1-[[(3-Iodo-2-propynyl)oxy]methoxy]-4-methoxy benzene can be synthesized by, for example, the method described in JP-B2-2852289.

1-Chloro-4-[[(3-iodo-2-propynyl)oxy]methoxy] benzene can be synthesized by, for example, the method described in JP-B-47-24121.

Zinc 2-pyridine thiol-1-oxide can be synthesized by, for example, the method described in U.S. Pat. No. 3,583,999.

Copper 2-pyridine thiol-1-oxide can be synthesized by, for example, the method described in JP-B2-3062825.

2-Pyridine thiol-1-oxide sodium salt can be synthesized by, for example, the method described in U.S. Pat. No. 4,396,766.

2,2-Dithio-bis(pyridine-1-oxide) can be synthesized by, for example, the method described in U.S. Pat. No. 3,892,760.

2-Methylthio-4-t-butyl amino-6-cyclopropyl amino-s-triazine can be synthesized by, for example, the method described in DE-A-1914014.

The proportion between 3-benzo[b]thiene-2-yl-5,6-dihydro-1,4,2-oxathiazine-4-oxide and compounds (a)-(m) in the antimicrobial compositions can be appropriately selected according to the types of target micro-organisms and the conditions under which above composition is to be used as an antimicrobial agent. Normally, the proportion between 3-benzo[b]thiene-2-yl-5,6-dihydro-1,4,2-oxathiazine-4-oxide and compounds (a)-(m) is, in weight ratio, in the range 20:1 to 1:20, preferably 5:1 to 1:5, and especially preferably 3:1 to 1:3.

The antimicrobial compositions of this invention can be used in a form that fits its purpose of use. For example, the antimicrobial compositions of this invention may be simply a mixture of 3-benzo[b]thiene-2-yl-5,6-dihydro-1,4,2-oxathiazine-4-oxide and compounds (a)-(m), but preferably it can include, besides 3-benzo[b]thiene-2-yl-5,6-dihydro-1,4,2-oxathiazine-4-oxide and compounds (a)-(m), an appropriate solvent and dispersant or carrier or other component.

The total content of 3-benzo[b]thiene-2-yl-5,6-dihydro-1,4,2-oxathiazine-4-oxide and compounds (a)-(m) in the composition of this invention varies with the product form and purpose of use, etc., but usually it is 0.1% by weight to 95% by weight, and preferably 0.2% by weight to 60% by weight, of the total antimicrobial compositions that is obtained.

The amount of the antimicrobial compositions of this invention to use varies with the composition and the type and concentration of the micro-organisms on which it is to be used, but generally, if it is to be used on fibre, paint, adhesive, etc., a good effect is obtained at about 1-10,000 mg/kg.

A.2. Solvents and Dispersants

If the system in which it is to be used is an industrial water system of any of various types, in consideration of the dissolvability and dispersibility of the effective components and other factors, it is desirable to prepare a liquid formulation that includes a solvent and dispersant, as discussed below.

As the solvent that can be used in the antimicrobial compositions of this invention, one may cite any solvent that does not adversely affect the active ingredients, for example, water, alcohols (for example, methyl alcohol, ethyl alcohol, ethylene glycol, propylene glycol, diethylene glycol, glycerin, etc.), ketones (for example, acetone, methyl ethyl ketone, etc.), ethers (for example, dioxane, tetrahydrofurane, cellosolve, diethylene glycol dimethyl ether, etc.), aliphatic hydrocarbons (for example, hexane, kerosene, etc.), aromatic hydrocarbons (for example, benzene, toluene, xylene, solvent naphtha, methyl naphthalene, etc.), halogenated hydrocarbons (for example, chloroform, carbon tetrachloride, etc.), acid amides (for example, dimethyl formadide, etc.), esters (for example, methyl acetate ester, ethyl acetate ester, butyl acetate ester, fatty acid glycerin ester, etc.), and nitrols (for example, acetonitrile, etc.). These solvents may be used either singly or in combination of two or more species.

As the dispersant that can be used in the antimicrobial compositions of this invention, one may cite any dispersant that does not adversely affect the active ingredients, for example, a surfactant. As such surfactants, one may cite soaps, high-grade alcohol sulfate ester, alkylsulfonic acid, alkyl allyl sulfonic acid, quaternary ammonium salt, oxyalkyl amine, fatty acid ester, polyalkylene oxide compounds, anhydrosorbitol compounds, etc. These dispersants may be used either singly or in combination of two or more species.

A.3. Carriers

As the carrier that can be used in the antimicrobial compositions of this invention, one may cite any dispersant that does not adversely affect the active ingredients, for example, clays (for example, kaolin, bentonite, acid clay, etc.), talcs (for example, talc powder, agalmatolite powder, etc.), silicas (for example, diatomaceous earth, silicic acid anhydride, mica powder, etc.), alumina, sulfur powder, activated charcoal, etc. These carriers may be used either singly or in combination of two or more species.

A.4. Other Components

The antimicrobial compositions of this invention may also contain other antimicrobial agents (for example, organic chlorine-based biocides, organic phosphorus-based biocides, organic iodine-based biocides, organic sulfur-based biocides, organic nitrogen-based biocides, organic nitrogen-sulfur-based biocides, benzimidazole-based biocides, phenol-based biocides, organic acid ester-based biocides, antibiotics, etc.), insecticides (for example, natural insecticides, carbamate-based insecticides, organic phosphor-based insecticides, etc.), adjuvants (for example, casein, gelatin, starch, alginic acid, agar, CMC, polyvinyl alcohol, vegetable oil, bentonite, cresol soap, etc.), degradation prevention agents, scents etc.

The antimicrobial compositions of the present invention may optionally further comprise quaternary ammonium salts such as quaternary ammonium salts of the trimethyl alkyl ammonium halide type, e.g. trimethyl decyl ammonium chloride, trimethyl dodecylammonium chloride, trimethyl tallow ammonium chloride, trimethyl oleyl ammonium chloride; or of the dimethyl alkyl benzyl ammonium type, e.g. dimethyl decyl benzyl ammonium chloride, dimethyldodecyl benzyl ammonium chloride, dimethyl hexadecylbenzyl ammonium chloride (commonly designated as "cetalkonium chloride"), dimethyl octadecyl benzyl ammonium chloride, dimethyl coco benzyl ammonium chloride, dimethyl tallow benzyl ammonium chloride; and particularly the dimethyl $C_{8-18}$alkyl benzyl ammonium chloride mixture which is commonly known as "benzalkonium chloride"; dimethyl dialkyl ammonium halides, e.g. dimethyl dioctyl ammonium chloride, dimethyl didecyl ammonium chloride, dimethyl didodecyl ammonium chloride, dimethyl dicoco ammonium chloride, dimethyl ditallow ammonium chloride, dimethyl octyl decyl ammonium chloride, dimethyl dodecyl octyl ammonium chloride, dimethyl dihydrogenated tallow ammonium chloride.

B. Target Organisms

The antimicrobial compositions of this invention are generally widely effective against bacteria, fungi, yeast, algae, etc., and it has an antimicrobial spectrum that is broader than that of antimicrobial compositions obtained by prescribing 3-benzo[b]thiene-2-yl-5,6-dihydro-1,4,2-oxathiazine-4-oxide or any of the compounds (a)-(m) singly. The antimicrobial compositions are inhibiting the growth or killing against the following organisms; bacteria such as *Bacillus, Staphylococcus, Enterobacter, Escherichia, Pseudomonas,* etc., fungi such as *Aspergillus, Aureobasidium, Chaetomium, Cladosporium, Gliocladium, Penicillium, Trichoderma,* etc., yeasts such as *Candida, Rhodotorula,* etc., and algae such as *Chlorella, Trentepohlia, Nostoc, Phormidium,* etc.

The antimicrobial compositions of this invention may be applied to various industrial products and industrial raw materials. As such various industrial products and industrial raw materials, one may cite fiber, paint, adhesive, wood, leather, processed paper products, electronic components, wall materials, resin moldings, etc.

WORKING EXAMPLES

By the following working examples, we describe in greater detail the antimicrobial effectiveness of the antimicrobial compositions of this invention. The term "MIC" as used in these working examples refers to the minimum inhibitory concentration (ppm) of the active ingredient in the antimicrobial compositions. More specifically, it refers to the minimum concentration of the mixture of 3-benzo[b]thiene-2-yl-5,6-dihydro-1,4,2-oxathiazine-4-oxide and compounds (a)-(m) in the antimicrobial compositions that is able to inhibit the growth of bacteria, fungi or algae.

Preparing Bacterial Suspensions for Inoculation

The bacterial suspensions for inoculation used in working example 1 were prepared as follows. Two bacteria, *Staphylococcus aureus* IFO 12732 and *Escherichia coli* IFO 3972, where inoculated respectively into two separate nutrient broth culture media, they were shake-cultured for 4-6 hours at 30° C., and two bacterial suspensions for inoculation were thus prepared.

Preparing Spore Suspensions for Inoculation

The spore suspensions for inoculation used in working example 2 were prepared as follows. Two fungi, *Aspergillus niger* IFO 6341 and *Penicillium funiculosum* IFO 6345, were cultured on two potato dextrose agar culture media not containing any biocides, and spores were formed. Next, said fungus spores were dispersed in disinfectant water to which 0.005% lubricant had been added, and two spore suspensions for inoculation were thus prepared.

Preparing Algae Suspensions for Inoculation

The algae suspensions for inoculation used in working example 3 were prepared as follows. Bold's Basal liquid culture medium (50 ml) was inoculated with *Chlorella pyrenoidosa* NIES 226, it was shake-cultured for 14 days at 25° C., and algae suspensions for inoculation was thus prepared.

Working Example 1

Antimicrobial compositions were prepared by adding 3-benzo[b]thiene-2-yl-5,6-dihydro-1,4,2-oxathiazine-4-oxide and compounds (a)-(m) to dimethyl sulfoxide in the weight ratios listed in Tables 1 and 2 below. Next, test culture media were prepared by adding each of the varying diluted aqueous solutions (0.2 ml) of the antimicrobial compositions to a nutrient broth culture medium (10 ml). Each of these test culture media was inoculated with the above bacterial suspensions for inoculation (0.1 ml), and after culturing for 24 hours at 30° C. Then, the presence or absence of bacteria growth was assessed by visually observing the turbidity of the culture medium. The minimum concentration of mixture of 3-benzo[b]thiene-2-yl-5,6-dihydro-1,4,2-oxathiazine-4-oxide and compounds (a)-(m) that was able to inhibit the growth of bacteria in the culture medium was taken as the MIC. Tables 1 and 2 list the MIC, for each bacterium, of the antimicrobial compositions of each weight ratio.

TABLE 1

| | Minimum inhibitory concentration (ppm) against *Staphylococcus aureus* | | | | |
|---|---|---|---|---|---|
| Components | 1:0 | 3:1 | 1:1 | 1:3 | 0:1 |
| A:a | 4 | 4 | 4 | 4 | 20 |
| A:b | 4 | 4 | 4 | 4 | 20 |
| A:c | 4 | 4 | 4 | 10 | 40 |
| A:d | 4 | 4 | 4 | 4 | 10 |
| A:e | 4 | 4 | 4 | 4 | 10 |
| A:f | 4 | 2 | 2 | 2 | 4 |

Note:
Compound A: 3-benzo[b]thiene-2-yl-5,6-dihydro-1,4,2-oxathiazine-4-oxide

TABLE 2

| | Minimum inhibitory concentration (ppm) against *Escherichia coli* | | | | |
|---|---|---|---|---|---|
| Components | 1:0 | 3:1 | 1:1 | 1:3 | 0:1 |
| A:a | 200 | 200 | 200 | 200 | 400 |
| A:b | 200 | 200 | 200 | 400 | 1000 |
| A:c | 200 | 40 | 40 | 40 | 40 |
| A:d | 200 | 100 | 100 | 100 | 200 |
| A:e | 200 | 100 | 100 | 100 | 200 |
| A:f | 200 | 20 | 10 | 10 | 10 |

Note:
Compound A: 3-benzo[b]thiene-2-yl-5,6-dihydro-1,4,2-oxathiazine-4-oxide

Working Example 2

Antimicrobial compositions were prepared by adding 3-benzo[b]thiene-2-yl-5,6-dihydro-1,4,2-oxathiazine-4-oxide and compounds (a)-(m) to dimethyl sulfoxide in the weight ratios listed in Tables 3 and 4 below. Next, test culture media were prepared by adding each of the varying diluted aqueous solutions (0.3 ml) of these antimicrobial compositions to a potato dextrose agar culture medium (15 ml). Each of these test culture media was inoculated with the above spore suspensions for inoculation (1 ml), and after culturing for 7 days at 28° C. Then, the presence or absence of fungus growth on each culture medium was observed visually. The minimum concentration of mixture of 3-benzo[b]thiene-2-yl-5,6-dihydro-1,4,2-oxathiazine-4-oxide and compounds (a)-(m) that was able to inhibit the growth of fungi on the culture medium was taken as the MIC. Tables 3 and 4 list the MIC, for each fungus, of the antimicrobial composition of each weight ratio.

TABLE 3

Minimum inhibitory concentration (ppm) against *Aspergillus niger*

| Components | 1:0 | 3:1 | 1:1 | 1:3 | 0:1 |
|---|---|---|---|---|---|
| A:a | 10 | 2 | 1 | 1 | 1 |
| A:b | 10 | 2 | 1 | 1 | 1 |
| A:c | 10 | 4 | 4 | 4 | 10 |
| A:d | 10 | 10 | 10 | 20 | 400 |
| A:e | 10 | 10 | 10 | 2 | 400 |
| A:f | 10 | 4 | 4 | 4 | 10 |
| A:h | 10 | 2 | 1 | 1 | 1 |
| A:i | 10 | 1 | 0.4 | 0.4 | 0.4 |

Note:
Compound A: 3-benzo[b]thiene-2-yl-5,6-dihydro-1,4,2-oxathiazine-4-oxide

TABLE 4

Minimum inhibitory concentration (ppm) against *Penicillium funiculosum*

| Components | 1:0 | 3:1 | 1:1 | 1:3 | 0:1 |
|---|---|---|---|---|---|
| A:a | 2 | 1 | 1 | 1 | 4 |
| A:b | 2 | 1 | 1 | 1 | 4 |
| A:c | 2 | 1 | 1 | 1 | 1 |
| A:d | 2 | 1 | 1 | 1 | 1 |
| A:e | 2 | 1 | 1 | 1 | 2 |
| A:f | 2 | 1 | 1 | 1 | 1 |
| A:h | 2 | 1 | 1 | 1 | 1 |
| A:i | 2 | 0.4 | 0.2 | 0.2 | 0.2 |

Note:
Compound A: 3-benzo[b]thiene-2-yl-5,6-dihydro-1,4,2-oxathiazine-4-oxide

Working Example 3

Antimicrobial compositions were prepared by adding 3-benzo[b]thiene-2-yl-5,6-dihydro-1,4,2-oxathiazine-4-oxide and compounds (a)-(m) to dimethyl sulfoxide in the weight ratios listed in Table 5 below. Next, test culture media were prepared by adding each of the varying diluted aqueous solutions (0.1 ml) of these antimicrobial compositions to Bold's Basal agar culture medium (15 ml). Each of these test culture media was inoculated with the above algae suspensions for inoculation (1 ml), and after culturing for 14 days at 25° C. and 1500 lux. Then, the presence or absence of algae growth on each culture medium was observed visually. The minimum concentration of mixture of 3-benzo[b]thiene-2-yl-5,6-dihydro-1,4,2-oxathiazine-4-oxide and compounds (a)-(m) that was able to inhibit the growth of algae on the culture medium was taken as the MIC. Table 5 lists the MIC, for algae, of the antimicrobial composition of each weight ratio.

TABLE 5

Minimum inhibitory concentration (ppm) against *Chlorella pyrenoidosa*

| Components | 1:0 | 3:1 | 1:1 | 1:3 | 0:1 |
|---|---|---|---|---|---|
| A:a | 40 | 10 | 10 | 10 | 10 |
| A:b | 40 | 10 | 10 | 10 | 10 |
| A:c | 40 | 20 | 20 | 20 | 20 |
| A:d | 40 | 40 | 40 | 40 | 100 |
| A:e | 40 | 20 | 20 | 20 | 40 |
| A:f | 40 | 20 | 10 | 10 | 10 |
| A:g | 40 | 0.2 | 0.1 | 0.1 | 0.1 |
| A:h | 40 | 20 | 20 | 20 | 40 |
| A:i | 40 | 20 | 20 | 20 | 20 |

Note:
Compound A: 3-benzo[b]thiene-2-yl-5,6-dihydro-1,4,2-oxathiazine-4-oxide

The results shown in Tables 1-5 show that the antimicrobial compositions of this invention, due to the synergistic effect of its active ingredients, have greater effectiveness and a broader antimicrobial spectrum than previous antimicrobial compositions. They also show that the concentration of an antimicrobial composition used for suppressing the same amount of bacteria, fungi, or algae is kept much lower than if an active ingredient is used singly.

EFFECTS OF THE INVENTION

This invention yields antimicrobial compositions comprising as their active ingredients 3-benzo[b]thiene-2-yl-5,6-dihydro-1,4,2-oxathiazine-4-oxide and one or more selected from (a) 1-[[(3-iodo-2-propynyl)oxy]methoxy]-4-methoxy benzene,
(b) 1-chloro-4-[[(3-iodo-2-propynyl)oxy]methoxy] benzene,
(c) Zinc 2-pyridine thiol-1-oxide,
(d) Copper 2-pyridine thiol-1-oxide,
(e) 2-pyridine thiol-1-oxide sodium salt,
(f) 2,2-dithio-bis(pyridine-1-oxide),
(g) 2-methylthio-4-t-butyl amino-6-cyclopropyl amino-s-triazine (irgarol),
(h) 3-iodo-2-propynyl butylcarbamate (IPBC),
(i) 2-(n-octyl)-3(2H)-isothiazolone (OIT), or
(j) 4,5-dichloro-2-(n-octyl)-3(2H)-isothiazolone (DCOIT)
(k) 2,4,5,6-tetrachloro-1,3-benzenedicarbonitrile (chlorothalonil)
(l) 1,1-dichloro-N-[(dimethylamino)sulfonyl]-1-fluoro-N-phenyl-methanesulfenamide (dichlofluanid)
(m) 1,1-dichloro-N-[(dimethylamino)sulfonyl]-1-fluoro-N-(4-methylphenyl)-methanesulfenamide (tolylfluanid).

Combining these active ingredients produces a synergistic effect of these components and provides antimicrobial compositions that are highly safe, are high effective, and have a broad antimicrobial spectrum. Furthermore, because the concentration of the active ingredients contained in the antimicrobial compositions of this invention is kept low, it can be prepared at very low cost and has little effect on the environment. The antimicrobial compositions of this invention are effective for antibacterial, antifungal and antialgal purposes on various industrial products and industrial raw materials.

What is claimed is:

1. An antimicrobial composition comprising 3-benzo[b]thiene-2-yl-5,6-dihydro-1,4,2-oxathiazine-4-oxide and one or more of the following compounds (a) 1-[[(3-iodo-2-propynyl)oxy]methoxy]-4-methoxy benzene,
(b) 1-chloro-4-[[(3-iodo-2-propynyl)oxy]methoxy] benzene,
(c) zinc 2-pyridine thiol-1-oxide,
(d) copper 2-pyridine thiol-1-oxide,
(e) 2-pyridine thiol-1-oxide sodium salt,
(f) 2,2-dithio-bis(pyridine-1-oxide),
(g) 2-methylthio-4-t-butyl amino-6-cyclopropyl amino-s-triazine,
(h) 3-iodo-2-propynyl butylcarbamate,
(i) 2-(n-octyl)-3(2H)-isothiazolone,
(j) 4,5-dichloro-2-(n-octyl)-3(2H)-isothiazolone,
(k) 2,4,5,6-tetrachloro-1,3-benzenedicarbonitrile,
(l) 1,1-dichloro-N-[(dimethylamino)sulfonyl]-1-fluoro-N-phenyl-methanesulfenamide or
(m) 1,1-dichloro-N-[(dimethylamino)sulfonyl]-1-fluoro-N-(4-methylphenyl)-methanesulfenamide, wherein the weight ratio of 3-benzo[b]thiene-2-yl-5,6-dihydro-1,4,2-oxathiazine-4-oxide and the compounds (a)-(m) is in the range 3:1 to 1:3.

2. A composition according to claim 1 wherein the total content of 3-benzo[b]thiene-2-yl-5,6-dihydro-1,4,2-oxathiazine-4-oxide and the compounds (a)-(m) is in the range of 0% by weight to 95%.

3. A composition according to claim 2 wherein the total content of 3-benzo[b]thiene-2-yl-5,6-dihydro-1,4,2-oxathiazine-4-oxide and the compounds (a)-(m) is in the range of 0.2% by weight to 60% by weight.

4. A method of protecting materials against bacteria, fungi, yeast, and algae, wherein the said method comprises administration or application of a composition according to claim 1.

5. A method of protecting materials against bacteria, fungi, yeast and/or algae wherein the method comprises administration or application of a composition according to claim 3.

* * * * *